(12) United States Patent
Wendt et al.

(10) Patent No.: US 10,609,493 B2
(45) Date of Patent: Mar. 31, 2020

(54) METHOD FOR ADJUSTING HEARING AID CONFIGURATION BASED ON PUPILLARY INFORMATION

(71) Applicant: Oticon A/S, Smørum (DK)

(72) Inventors: Dorothea Wendt, Smørum (DK); Thomas Lunner, Smørum (DK); Patrycja Książek, Amstelveen (NL); Emina Alickovic, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 16/180,818

(22) Filed: Nov. 5, 2018

(65) Prior Publication Data

US 2019/0141458 A1    May 9, 2019

(30) Foreign Application Priority Data

Nov. 6, 2017   (EP) .................................... 17200112

(51) Int. Cl.
*H04R 25/00*       (2006.01)
*A61B 3/11*         (2006.01)
(Continued)

(52) U.S. Cl.
CPC .............. *H04R 25/30* (2013.01); *A61B 3/112* (2013.01); *A61B 5/048* (2013.01); *A61B 5/121* (2013.01);
(Continued)

(58) Field of Classification Search
CPC ....... A61B 5/0478; A61B 5/048; A61B 5/121; A61B 5/4836; A61B 5/6817; G06F 3/013
(Continued)

(56) References Cited

U.S. PATENT DOCUMENTS 3,799,146 A * 3/1974 John .................... A61B 5/0484
                                                    600/544
5,003,986 A * 4/1991 Finitzo ............... A61B 5/04845
                                                    600/544

(Continued)

*Primary Examiner* — Walter F Briney, III
(74) *Attorney, Agent, or Firm* — Birch, Stewart, Kolasch & Birch, LLP

(57) ABSTRACT

The disclosure presents a hearing device system and a method for adjusting hearing aid configuration, where a user is wearing a hearing device, the method comprising transmitting a first background sound signal to the hearing device, transmitting a first sound pattern to the hearing device, evaluating, via a camera unit, a first pupillary information of a first eye of the user in response to a first sound scene comprising the first background sound signal and the first sound pattern. The evaluating may be repeated providing at least a second pupillary information of the first eye of the user in response to a second sound scene being different from the first sound scene, and where an averaged pupillary information is provided based on an average between the first pupillary information and at least the second pupillary information, and selecting a pupillary fitting model based on the averaged pupillary information, determining a first parameter and at least a second parameter of the pupillary fitting model based on the averaged pupillary information, classifying the averaged pupillary information into either a first category or at least a second category based on the first parameter and the at least second parameter, and wherein the hearing aid configuration is adjusted if the averaged pupillary information is in the first category, and the hearing aid configuration is not adjusted if the averaged pupillary information is in the second category.

18 Claims, 11 Drawing Sheets

(51) Int. Cl.
*A61B 5/048* (2006.01)
*A61B 5/12* (2006.01)
*A61B 5/00* (2006.01)
*G06F 3/01* (2006.01)
*H04R 27/00* (2006.01)
*A61B 5/0478* (2006.01)
*A61B 5/0484* (2006.01)

(52) U.S. Cl.
CPC .......... *A61B 5/4836* (2013.01); *A61B 5/6817* (2013.01); *G06F 3/013* (2013.01); *H04R 25/40* (2013.01); *H04R 25/505* (2013.01); *H04R 25/70* (2013.01); *A61B 5/0478* (2013.01); *A61B 5/04845* (2013.01); *A61B 5/6867* (2013.01); *H04R 25/507* (2013.01); *H04R 25/552* (2013.01); *H04R 25/554* (2013.01); *H04R 25/606* (2013.01); *H04R 27/00* (2013.01); *H04R 2225/43* (2013.01); *H04R 2225/55* (2013.01); *H04R 2225/61* (2013.01); *H04R 2225/67* (2013.01)

(58) Field of Classification Search
USPC ..................... 381/312, 314; 607/55–57, 137
See application file for complete search history.

(56) References Cited

U.S. PATENT DOCUMENTS

| | | | |
|---|---|---|---|
| 5,243,686 A * | 9/1993 | Tokuda | G10L 15/02 704/200 |
| 9,498,138 B2 * | 11/2016 | Zuckerman-Stark | G16H 50/30 |
| 2009/0285456 A1 * | 11/2009 | Moon | G06K 9/00335 382/118 |
| 2010/0076339 A1 * | 3/2010 | Marcoux | A61B 5/04845 600/559 |
| 2010/0196861 A1 * | 8/2010 | Lunner | H04R 25/505 434/112 |
| 2013/0121496 A1 | 5/2013 | Boretzki | |
| 2014/0146987 A1 * | 5/2014 | Pontoppidan | H04R 25/30 381/314 |
| 2014/0186806 A1 | 7/2014 | Hallowell et al. | |
| 2014/0358010 A1 * | 12/2014 | Battiwalla | A61B 5/4851 600/476 |
| 2014/0369537 A1 * | 12/2014 | Pontoppidan | A61B 5/165 381/314 |
| 2016/0119726 A1 | 4/2016 | Pontoppidan et al. | |
| 2019/0090073 A1 * | 3/2019 | Wendt | A61B 3/112 |
| 2019/0146580 A1 * | 5/2019 | Baugh | G06F 3/013 351/204 |

* cited by examiner

Sound pattern (3, 3A, 3B)

| Sentence length | Linguistic complexity (15) | First sound level | 16A |
|---|---|---|---|
| Speech sample/Speech corpus (14) | | | 13 |

Fig. 5A

Background sound signal (2, 2A, 2B)

| Sample length = Sentence length | Second sound level | 16B |
|---|---|---|
| Tone/sound/speech sample (14) | | 17 |

Fig. 5B

Sound scene (5, 5A, 5B)

| Sound pattern | Background sound signal |
|---|---|
| 3, 3A, 3B | 2, 2A, 2B |

Fig. 5C

METHOD FOR ADJUSTING HEARING AID CONFIGURATION BASED ON PUPILLARY INFORMATION

TECHNICAL FIELD

The disclosure relates to a hearing device system and a method for adjusting hearing aid configuration, such as hearing aid settings, optimal mapping parameters of stimulation electrodes connected to a cochlear implant, where the hearing device is a cochlear implant, placement of an ear piece of the hearing device into an ear canal and/or frequency response of the hearing device.

BACKGROUND

Modern hearing aids require configuration to match specific hearing loss, physical features, and lifestyle of the wearer. This process is called "fitting" and is typically performed by audiologists who treat persons with hearing loss and proactively prevents related damage. The fitting and fine-tuning of hearing aids today is not evidence based, as audiometric tests used today in essence are based on self-reported data. This is also true for the outcome data on hearing aid satisfaction as they are based on self-reported questionnaires. Self-reported data can be prone to several biases, such as recall bias, prestige bias, and misclassification bias, which can all cloud the outcome measure's reliability and validity and thus can hinder evidence based clinical decision support. Moreover, traditional audiometric tests used in the clinic today can have limitations as tone detection in the brain does not solely reflect how good speech is perceived, and how speech perception requires listening effort. Fitting to the audiometric tests does also not take into account individual cognitive efforts and problems in processing the sounds encountered.

Thus, there is a need for improvements in the technical field of hearing aid fitting/adjustment.

SUMMARY

An object of the present disclosure is to provide a method and a hearing device system with improved adjustment capability of hearing aid configuration.

A further object of the present disclosure is to provide a method and a hearing device system with improved fitting capability of hearing aid setting and/or hearing profile of a user of the hearing aid.

An even further object of the present disclosure is to provide a method for improving the capability of a hearing care professional to evaluate whether the hearing aid configuration is suitable for the user of the hearing device.

The hearing device may be a hearing aid, a cochlear implant, a headset, a headphone or a speaker.

Objects of the present disclosure are achieved by the present disclosure described in the accompanying claims and as described in the following.

An object of the present disclosure is achieved by a method for adjusting hearing aid configuration, where a user is wearing a hearing device. The method may comprise transmitting a first background sound signal to the hearing device. The background signal, i.e. the first background sound signal, may comprise a speech weighted un-modulated noise sound, a speech weighted modulated noise sound, a single competing talker sound or a multiple competing talkers sound. The method may include multiple background sound signal.

The method may further comprise transmitting a first sound pattern to the hearing device, where the first sound pattern may comprise a speech sample, such as a speech corpus The speech corpus may be stored in a memory of a smartphone, the hearing device, a computer or a server (e.g. a cloud server). The speech corpus may either be a read speech corpus or a spontaneous speech corpus.

The read speech corpus may for example be a book excerpts, a broadcast news, a list of words, a list of sentences or a sequences of numbers.

The spontaneous speech corpus may for example be dialog—between two or more people (includes meetings), narratives—a person telling a story, map-tasks—one person explains a route on a map to another; appointment-tasks—two people try to find a common meeting time based on individual schedules.

Alternatively, the speech corpus may include everyday sentences, such as;
  Hearing in noise test,
  Matrix sentences (Kollmeier et al, 2014),
  American sign language sentences (ASL sentences),
  IEEE sentences
  SPIN sentences
  Göttingen sentences
  HSM sentences
  DAT sentences
  CRM sentences The speech sample may be defines as having a sample length in time and in number of words, a linguistic complexity and a sound level. The linguistic complexity refers to the amount of discourse (oral or written), the types and variety of grammatical structures, the organization and cohesion of ideas and, at the higher levels of language proficiency, the use of text structures in specific genres. The linguistic may be measured by using linguistic sequence complexity (LC) which is a measure of the 'vocabulary richness' of a genetic text in gene sequences, e.g. the speech sample.

The method may further comprise evaluating, via a camera unit, a first pupillary information of a first eye of the user in response to a first sound scene comprising the first background sound signal and the first sound pattern. The camera unit may be configured to focus on one or both of the eyes of the user of the hearing device and record their movement and/or change in the pupil dilation and/or pupil size. The camera may use the center of the pupil and infrared/near-infrared non-collimated light to create corneal reflections (CR), for example. The pupillary information may comprise a measure of the pupil dilation and/or the pupil size within a speech sample time which corresponds to the length in time of the first sound pattern, i.e. the speech sample.

The method may comprises evaluating via multiple camera units. For example, a goggle or alike can comprise one or more camera units and one or more IR radiation sources.

In some examples, the person's pupils can be evaluated automatically, for instance by using an automatic eye tracking camera device, being the camera unit, and/or a pupilometer, being the camera unit, for measuring the person's pupil dilation as an indicator of their cognitive load or listening effort.

An additional or alternative the camera unit can be part of a portable, handheld device that may provide a reliable and objective measurement of pupillary size, and reactivity through measurement of the pupil dilation.

Additionally, in the method the evaluating may be repeated providing at least a second pupillary information of the first eye of the user in response to a second sound scene being different from the first sound scene, and where an averaged pupillary information is provided based on an average between the first pupillary information and at least the second pupillary information.

The evaluating may be repeated a plurality of times measuring a plurality of pupillary is information in response to different sound scenes. The different sound scenes may be different in such a way that the speech corpus of the sound pattern, e.g. the first sound pattern and the second sound pattern, may be different by the linguistic complexity, the sample length of the sound pattern are the same and the background sound signal may be the same for each scene.

The first sound pattern and/or the second sound pattern may be configured into following conditions; a first condition, the sound pattern has a first speech recognition threshold and no noise reduction from the hearing device, wherein the speech recognition threshold (SRT) may indicate the speech recollection accuracy. SRT set to for example 50% accuracy or less may be classified as a noisy situation, and if SRT is set to about 95% accuracy may be classified as an ecological situation. In the first condition the first speech recognition threshold may be set to 50% accuracy. A second condition, the sound pattern has a second speech recognition threshold being larger than the first speech recognition threshold, and no noise reduction from the hearing device. The second speech recognition threshold may be to 95% accuracy. A third condition, the sound pattern has the first speech recognition threshold and with noise reduction from a noise reduction algorithm applied in the hearing device. A fourth condition, the sound pattern has the second speech recognition threshold being larger than the first speech recognition threshold, and with noise reduction from the noise reduction algorithm applied in the hearing device. The first scene and/or the second sound scene may comprise the first sound pattern or the second sound pattern, or another sound pattern, being configured to the first, second third or fourth condition.

The SRT of the sound scene may be depending on a noise level in the background sound signal and/or based on the first sound level and/or the second sound level.

Alternatively, the method may via a first camera unit evaluate a first pupillary information of the first eye of the user, and via a second camera unit evaluate a first secondary pupillary information of a second eye of the user. Thereby, the method and a hearing device system including the method may be configured to use either the first pupillary information or the first secondary pupillary information based on a quality measure of the first pupillary information and a quality measure of the first secondary pupillary information for determine the average pupillary information. The quality is for example depended on the blinking rate, movement of the eye or other artifacts which acts as noise to the pupillary information. A correlation between the first pupillary information and the first secondary pupillary information may be determined. The correlation may be used for determine the quality of the first pupillary information and/or the first secondary pupillary information. A low correlation may indicate that the measure of the first pupillary information and/or the first secondary pupillary information is not that representative of the cognitive load/listening effort of the user wearing the hearing device, i.e. the quality of the pupillary information is low. A high correlation may indicate that the measure of the first pupillary information and/or the first secondary pupillary information is well representative of the cognitive load/listening effort of the user wearing the hearing device, i.e. the quality of the pupillary information is good enough to be used for determine the average pupillary information.

The hearing device system may comprise a second camera unit and a quality estimator unit which is configured to determine the quality of the first pupillary information and the first secondary pupillary information.

The method may further comprise selecting a pupillary fitting model based on the averaged pupillary information. The pupillary fitting model may be based on a polynomial fit model, a growth curve analysis model, a spline fit model, Bayesian model, or a system identification model.

Different pupillary fitting model may be used for different time periods of the speech sample time. The speech sample time may be divided into multiple time periods, and wherein in each time period a different pupillary fitting model is used. Thereby, you obtain a more precise fitting of the average pupillary information.

The selection of the pupillary fitting model may be done based on the shape of the pupillary profile of the average pupillary information, wherein the pupillary profile comprises the pupil dilation or the pupil size as a function of the speech sample time.

The selection of the pupillary fitting model may be done automatically and/or continuously by choosing a pupillary fitting model which has the lowest Root mean-squared (RMS) residual errors. The method may select a first pupillary fitting model and provided onto the average pupillary information for determining a first RMS residual error, i.e. the RMS residual error expresses how good or how bad the selected pupillary fitting model is fitted to the pupillary profile. A low RMS residual error indicates a good correlation between the selected pupillary fitting model and the pupillary profile, and a high RMS residual error indicates a poor correlation between the selected pupillary fitting model and the pupillary profile. A second pupillary fitting model is selected and provided onto the average pupillary information for determining a second RMS residual error. A number of different pupillary fitting models are chosen and a number of RMS residual error are calculated for each pupillary fitting model. The pupillary fitting model with the lowest RMS residual error is selected, i.e. the lowest RMS residual error indicates that the selected pupillary fitting model represents best the pupillary profile.

Additionally, the method may comprise determining a first parameter and at least a second parameter of the pupillary fitting model based on the averaged pupillary information.

The first parameter and the at least second parameter may for example be a first coefficient and a second coefficient of a polynomial fitting model, or the first parameter may be the constant and the at least second parameter may be a slope coefficient of a linear fitting model. Thereby, the first parameter and the at least second parameter may be the coefficients and/or constants within a pupillary fitting model which may be changed automatically and/or continuously in order to provide a representation of the pupillary profile based on the pupillary fitting model.

Furthermore, the method may comprise classifying the averaged pupillary information into either a first category or at least a second category based on the first parameter and the at least second parameter. In general, the classification may include determining a category threshold separating the first category and the second category.

In one example, the category threshold may be determined by a plurality of relations between a first parameter and at least a second parameter after N times iterations of the disclosed method.

The classification of the averaged pupillary information may be supported or provided by a support vector machine scheme.

Alternatively, the classification of the averaged pupillary information may be supported or provided by a neural network or a deep neural network and based on the first parameter and the at least second parameter.

Furthermore, the classification of the averaged pupillary information may be supported or provided by a discriminant function analysis and based on the first parameter and the at least second parameter.

The classification of the averaged pupillary information may be supported or provided by Gausssian mixture model, Hidden markov model, Nearest neighbor classifier or Linear regression.

The classification may be based on one of the following classifier:
1. Multi-Scale Principal Component Analysis (MSPCA):
   a. Aminghafari, M.; Cheze, N.; Poggi, J-M. (2006), "Multivariate de-noising using wavelets and principal component analysis," Computational Statistics & Data Analysis, 50, pp. 2381-2398.
   b. Bakshi, B. (1998), "Multiscale PCA with application to MSPC monitoring," AIChE J., 44, pp. 1596-1610.
2. Wavelets:
   a. Daubechies, I. (1992), Ten lectures on wavelets, CBMS-NSF conference series in applied mathematics. SIAM Ed.
   b. Mallat, S. (1989), "A theory for multiresolution signal decomposition: the wavelet representation," IEEE Pattern Anal. and Machine Intell., vol. 11, no. 7, pp 674-693.
3. Kalman Filter:
   a. Gustafsson, Fredrik. (2010), Statistical sensor fusion. Studentlitteratur.
   b. Gustafsson, Fredrik. (2000), Adaptive filtering and change detection. Vol. 1. New York: Wiley.
4. Decision Tree Based Classifiers:
   a. General reference: Witten I H, Eibe F, Hall M A. Data Mining: Practical Machine Learning Tools and Techniques. Thirdth. Morgan Kaufmann, San Francisco; 2011
   b. C 4.5:
      i. J. Ross Quinlan. 1993. C4.5: Programs for Machine Learning. Morgan Kaufmann Publishers Inc., San Francisco, Calif, USA.
   c. Random Forest:
      i. Breiman, Leo. Random forests. Machine learning, 2001, 45.1: 5-32.
      ii. LIAW, Andy, et al. Classification and regression by randomForest. R news, 2002, 2.3: 18-22.
   d. Random Tree:
      i. Witten I H, Eibe F, Flail M A. Data Mining: Practical Machine Learning Tools and Techniques. Thirdth. Morgan Kaufmann, San Francisco; 2011C 4.5.
   e. Kernel and Sparse kernel based classifiers (including SVM, ANN, Linear, Logistic and Gaussian Regression):
      i. General reference: Bishop, Christopher M. Pattern recognition and machine learning. springer, 2006.
5. Ensemble machine learning algorithm:
   a. Rotation Forest:
      i. RODRIGUEZ, Juan Jose; KUNCHEVA, Ludmila I.; ALONSO, Carlos J. Rotation forest: A new classifier ensemble method. IEEE transactions on pattern analysis and machine intelligence, 2006, 28.10: 1619-1630.

The method may then adjust the hearing aid configuration if the averaged pupillary information is in the first category, and the hearing aid configuration is not adjusted if the averaged pupillary information is in the second category.

The adjustment of the hearing aid configuration may for example imply an adjustment of hearing aid settings, such as the gain at different frequencies of a hearing profile of a hearing aid worn by the user of the hearing aid and/or the treble.

Alternatively, the adjustment of the hearing aid configuration may for example imply an adjustment of an equalizer of the hearing aid, such as the gain or the treble of an audio signal generated by a microphone of a hearing aid based on an acoustical signal received by the microphone.

The hearing aid configuration may imply settings of noise reduction algorithm, anti-feedback filtering or processing, or other types of acoustical processing of the acoustical signal received by the microphone of the hearing aid.

Furthermore, the adjustment of the hearing aid configuration may for example imply a continuously and/or an automatically adjustment of the hearing aid settings according to an acoustic environment detected by the hearing aid or a microphone unit (e.g. in a smartphone) configured to be connected to the hearing aid. For example, the user may wear a goggle which includes a camera unit for tracking at least the first eye or the user may have a smartphone which includes a camera unit configured to track at least the first eye when the user pulls out the smartphone and points the camera unit towards the at least first eye. Then, when the user is entering an acoustic environment which is difficult for the hearing aid to process into an acoustic sound which is listenable and understandable for the hearing impaired user, then the user is able to automatically adjust the hearing aid settings when initiating an application installed on the smartphone and pointing the camera unit to the at least first eye, and wherein the application is configured to initiate the disclosed method which is then being computed or processed on the smartphone, in the hearing aid, or in a server located remotely from the user and which is connected to either the smartphone or the hearing aid. In this example, the user will be able to automatically adjust the hearing aid configuration, e.g. the hearing aid setting, according to the acoustic environment. In the situation where the user is wearing the goggle, then the method is being continuously initiated or initiated when the pupil size or the pupil dilation is above a certain threshold. Then, when the method is being continuously initiated via the pupillary information received by the goggle, then the hearing aid configuration, e.g. the hearing aid setting, will always be optimal adjusted to the acoustic environment of the user. The computing or the processing of the method will be initiated by an application installed on a smartphone, the goggle or the hearing aid, and the computing or the processing of the method will take place in the smartphone, the goggle, the hearing aid or in a server located remotely from the user and which is connected to either the smartphone, the goggle or the hearing aid.

The adjustment of the hearing aid configuration may be provided by a hearing care professional based on the classification of the average pupillary information into either the first category or in the second category. In this example, the user may either be placed remotely or close to the hearing care professional (HCP) wearing the hearing device. In the case where the user is placed remotely, then the communication between the HCP and a user may be done via a communication network, such as a telephone network, a speaker/microphone system, internet, IP telephone, Bluetooth or WIFI etc. In the case where the user is placed close to the HCP, then the communication is done mouth to mouth. In this example, the HCP receives objectively measures of the user's response to the proposed hearing aid configuration, e.g. the hearing aid setting, in the form of the averaged pupillary information being categorized. Every time the HCP adjust one hearing aid setting and initiate the computing or the processing of the method on a processing device, such as a computer, a laptop, a tablet etc., the HCP will get a new classification of the averaged pupillary information, and based on the classification, the HCP will know whether to adjust the hearing aid setting once again or whether the hearing aid setting is suitable for the user of the hearing aid. The adjustment of the hearing aid configuration could also be the adjustment of the configuration of stimulation electrodes connected to a cochlear implant, where the purpose of adjusting the configuration of the stimulation electrodes will be to determine ECAP threshold levels and ECAP comfortable levels.

The adjusting of the hearing aid configuration may be based on the first parameter and the at least second parameter of the fitting model or based on a relation between the first parameter and the at least second parameter. For example, an amount of gain or treble to be adjusted may be in correlation with the first parameter and/or the at least second parameter or with the relation between the first parameter and the at least second parameter.

Thereby, the hearing device system may be able to automatically adjust the hearing aid configuration based on the parameters.

The Fitting model may imply more than two parameters, such as three, four, five or six parameters, corresponding to for example a second order, a third order, a fourth order, a fifth order or a sixth order polynomial fitting model.

The second sound scene may comprise a combination of a second background sound signal received by the hearing device and the first sound pattern or a combination of a second sound pattern received by the hearing device and the first background sound signal, or a combination of the first background sound signal and the second sound pattern.

The second sound scene may be different from the first scene in such a way the response of the user's first eye and/or the second eye will be different causing a change in the pupillary information, such as the second pupillary information or a normalized second pupillary information.

A plurality of sound patterns and/or a plurality of background sound signals may be transmitted to the hearing device. and the method may repeat relevant steps in order to provide new pupillary information or new normalized pupillary information, such as a third pupillary information, a fourth pupillary information and etc. or such as a normalized third pupillary information, a normalized fourth pupillary information and etc., and then to provide a new average pupillary information and a categorization of the new average pupillary information based on the plurality of sound patterns and/or a plurality of background sound signals.

The plurality of sound patterns may be the same or different with respect to the speech content of the speech corpus or the length of the speech content or the sound level of the speech content. The plurality of background sound signals may be the same or different with respect to whether the background sound signal is a speech sound, tones, spontaneous sounds or any sounds which is assumed as noise by the user.

The method may comprise performing a baseline measurement, via the camera unit, which includes a measurement of a first baseline pupillary information of the first eye of the user in response to the first background sound signal.

The method may comprise pre-processing the first pupillary information and the first baseline pupillary information for removing artifacts in the first pupillary information and the first baseline pupillary information, and providing a normalized first pupillary information based on normalization of the first pupillary information with the first baseline pupillary information. The artifacts may for example be eye blinking, eye movement which prevents the camera unit to monitor the pupil. BY removing the artifacts improves the quality of the measured pupillary information.

The method may then repeat the pre-processing of at least the second pupillary information in response to the second sound scene and of at least a second baseline pupillary information, wherein the second baseline pupillary information is provided in response to a second background sound signal and a second baseline measurement, and providing a normalized second pupillary information based on a normalization of the second pupillary information with the second baseline pupillary information, and wherein the averaged pupillary information is provided based on an average between the normalized first pupillary information and at least the normalized second pupillary information.

The baseline measurement and/or the pre-processing may be repeated numerous of times with different sound scenes in order to obtain a more reliable measure of the cognitive load or listening effort via the average pupillary information.

The second baseline pupillary information is provided by the camera unit.

The pre-processing may comprise alignment in time the sound scenes by interpolating a time length of each of the sound scene onto a reference time vector in order to remove any differences in the time length of each of the sound scene, and filtering the sound scenes being aligned in time for removing high frequency artifacts from the sound scenes.

The second sound scene may comprise the combination of the second background sound signal received by the hearing device and the first sound pattern or the combination of the second sound pattern received by the hearing device and the first background sound signal, or the combination of the first background sound signal and the second sound pattern.

The second background sound signal may be the same or different from the first background sound signal.

The background sound signals, such as the first background sound signal and the second background sound signal, comprise a background sample configured with a sample length in time, and/or a sound level, and wherein the background sample comprises a background speech sample, a tone signal, a synthesized acoustic signal, and/or an acoustical environment sound.

The sound scene for each iteration of the method in order to determine pupillary information and/or baseline pupillary information may be different in order to keep the concentration of the user wearing the hearing device through N times of iteration of evaluating the first eye and/or pre-processing of the pupillary information and/or baseline pupillary information.

The background sound signal in each sound scene may be different and the sound pattern may for example be different for each sound scene in order to attract the user's attention during the N times of evaluations of the first/second eye of the user.

The N times may be between 5 and 10 times, 10 and 20 times, 20 and 25 times or 5 and 25 times. For example, if N is 20 then the averaged pupillary information may be based on 20 pupillary information or 20 normalized pupillary information including 20 sound scenes where each sound scene is different.

The method may comprise detecting eye-blinks in the pupillary information and in the baseline pupillary information, where the pupillary information and the baseline pupillary information comprises data of pupil size and/or pupil dilation of the first eye, and the eye-blinks are detected as a value of the pupil size being below a pupil size threshold. The method may further include removing the pupil sizes being below the pupil size threshold from the pupillary information and the baseline pupillary information, and interpolating the remaining pupil size, i.e. the pupil size not being removed. The pupil size threshold may be between 2 and 3 standard deviation, between 2.5 and 3.5 standard deviation or 3 standard deviation, where standard deviation is defined as a quantity expressing by how much the pupil size differ from the mean value for the pupil size.

The advantage of detecting and removing eye-blinks is that the correlation between the average pupillary information and the cognitive load or listening effort of the user wearing the hearing device/hearing aid will be more precise since eye-blinks, i.e. the artifact, will not disturb the process of determine the first and the second parameter of the pupillary fitting model.

The evaluation and/or the pre-processing may be repeated N times with different sound scenes, such as the first sound scene and the second sound scene and another sound scene. N may be determined based on the quality of the evaluation of the pupillary information, such as the first pupillary information or the second pupillary information or other pupillary information in response to a sound scene. The quality of the evaluation may be determined by how noisy the pupillary information is defined by the number of removed measured pupil sizes/dilations in the pupillary information and/or in the baseline pupillary information. The removing of the measured pupil sizes and/or dilations from the pupillary information may be due to for example eye-blinking or movement of the first eye and/or the second eye.

The pre-processing may comprise alignment in time the sound scenes by interpolating a time length of each of the sound scene onto a reference time vector in order to remove any differences in the time length of each of the sound scene, and removing high frequency artifacts from the sound scenes by a moving average filter. The moving average filter may be a low pass filter that is used for smoothing the pupillary information, such as pupil data/signal (e.g. pupil size or pupil dilation).

The reference time vector may be the sample length in time of the sound scenes which is longest. The sound scenes are used for evaluating the pupillary information.

The averaged pupillary information may be an average of N times of pupillary information or N times of normalized pupillary information provided by N times of evaluation of the first eye and/or the second eye of the user in response to N times of sound scenes where the sound pattern or the background sound signal in each sound scene are different.

The measure of the baseline measurement and the evaluating of the pupillary information in response to a sound scene may be performed on the first eye and the second eye of the user. The advantage of using both eyes of the user is that if the evaluation of the first eye provides pupillary information which is too noisy then the second eye may provide pupillary information which is less noisy, and thereby, more suitable for determine the listening effort or the cognitive load in response to the sound scene.

A further object of the present disclosure is to obtain a hearing device system for adjusting hearing aid configuration. The hearing device system may comprise a hearing device configured to receive a first background sound signal, and where the hearing device receives a first sound pattern, a camera unit configured to evaluate a first eye of the user in response to a first sound scene comprising the background sound signal and the first sound pattern and providing a first pupillary information based on the first sound scene, and wherein the camera unit is further configured to repeat the evaluation of the first eye of the user and provide at least a second pupillary information of the first eye of the user in response to a second sound scene being different from the first sound scene. The hearing device system may further comprise a processing unit configured to provide an averaged pupillary information based on an average between the first pupillary information and at least the second pupillary information, a fitting model unit configured to select a pupillary fitting model based on the averaged pupillary information, and the fitting model is further configured to determine a first parameter and at least a second parameter of the pupillary fitting model based on the averaged pupillary information. Additionally, the hearing device may comprise a classifier unit configured to classify the averaged pupillary information into either a first category or at least a second category based on the first parameter and the at least second parameter, and wherein the hearing aid configuration may be adjusted if the averaged pupillary information is in the first category, and the hearing aid configuration is not adjusted if the averaged pupillary information is in the at least second category.

The hearing device system may for example be used as a tool for determine whether the hearing aid configuration is properly determined for the user of the hearing device.

Furthermore, the hearing device system may be used as a fitting tool to provide remote fitting of the hearing aid configuration or to provide fine-adjustment of hearing aid settings.

The camera unit may be configured to perform a baseline measurement, which includes a measurement of a first baseline pupillary information of the first eye of the user in response to the first background sound signal, and wherein the processor unit is configured to perform pre-processing of the first pupillary information and the first baseline pupillary information for removing artifacts in the first pupillary information and the first baseline pupillary information, provide a normalized first pupillary information based on normalization of the first pupillary information with the first baseline pupillary information, repeat the pre-processing with at least a second baseline pupillary information in response to a second background sound signal and at least the second pupillary information in response to the second sound scene, provide a normalized second pupillary information, and provide the averaged pupillary information based on an average between the normalized first pupillary information and at least the normalized second pupillary information.

The processor unit may be configured to detect eye-blinks in the pupillary information and in the baseline pupillary information, where the pupillary information and the baseline pupillary information comprises data of pupil size and/or pupil dilation of the first eye, and the eye-blinks are detected as a value of the pupil size being below a pupil size threshold, remove the pupil sizes being below the pupil size threshold from the pupillary information and the baseline pupillary information, and interpolate the removed pupil size.

The classifier unit may comprise a support vector machine configured to classify the averaged pupillary information based on the relation between the first parameter and the at least second parameter.

The hearing aid configuration may include hearing aid settings, optimal mapping parameters of stimulation electrodes connected to a cochlear implant, where the hearing device is a cochlear implant, placement of an ear piece of the hearing device into an ear canal, and/or frequency response of the hearing device.

The hearing device system comprising;
the hearing device configured to determining sound pressure level, modulation depth and modulation frequency over time of a background sound signal, such as the first background sound signal,
stimulation electrodes configured to stimulate a cochlear of a user of the hearing device based on a sound scene, such as the first sound scene, including both the background sound signal and the sound pattern received by the hearing device,
the camera unit,
the classifier unit is further configured to estimate whether the user of the hearing device has identified speech or not by;
determining when a speech was present in the sound scene,
analyzing the averaged pupillary information provided by the processing unit and a latency in relation to the sound scene,
combining the information of when the speech was present in the sound scene, the averaged pupillary information and the latency, and providing a measure of speech identification, of the user, or a likelihood of the speech having been identified, of the user,
classifying the averaged pupillary information into the first category or at least the second category based on the measure of speech identification or the likelihood of the speech having been identified.

To improve validity, the classifier unit includes an optional calibration mode which asks the user to input the speech either verbally or through a graphic user interface.

For example, a two-year-old child with hearing loss and with an expressive language delay recently received cochlear implants. The audiologist plays pre-recorded simple words to the child (e.g., dog, house, baby) and measures whether the child identifies these words without the child needing to repeat back the words. The audiologist uses this information to trial different cochlear implant mapping parameters, to find the parameters that lead to optimal speech identification. The audiologists save the optimal parameters in the cochlear implant for daily use.

A further example, as part of a job recruitment process, the user may be tested for her proficiency in German, her second language. The job interviewer talks to the user in German using words and sentences that user is likely to encounter as part of the job. The job interviewer can quickly and reliably see which percentage of such conversations Mary can identify.

The system could also be tested in a scenario where the stimuli component extends beyond speech stimuli to non-speech stimuli. For example, the system could be used to measure detection of sounds for audiometry (hearing assessment) either without hearing devices or with hearing devices.

The hearing device system may include a hearing aid configuration unit configured to receive a classifier signal comprising the averaged pupillary information and/or a category, such as the first category or the second category, of the averaged pupillary information, wherein the hearing aid configuration unit is configured to automatically and/or continuously adjust the hearing aid configuration based on the category and/or the averaged pupillary information received via the classifier signal.

The hearing device system may comprise a second camera unit and a quality estimator unit which may be configured to determine the quality of the first pupillary information and the first secondary pupillary information.

The processing unit may be configured to select different fitting model for different time periods of the pupillary profile comprised by the averaged pupillary information.

BRIEF DESCRIPTION OF DRAWINGS

The objects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each object may each be combined with any or all features of the other objects. These and other objects, features and/or technical effect will be apparent from and elucidated with reference to the illustrations described hereinafter in which:

FIGS. 5A, 5B and 5C, illustrate the sound pattern, the background sound signal and sound scene, respectively.

DETAILED DESCRIPTION

Figure 1:
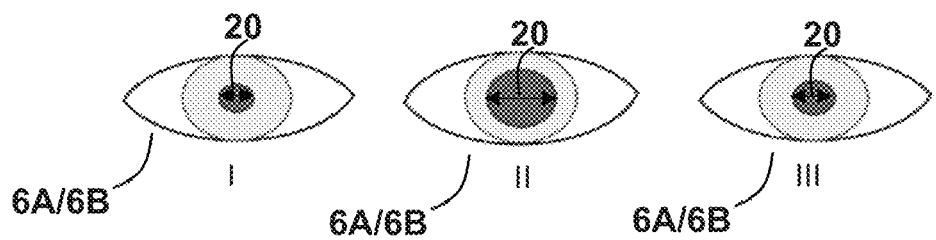
FIG. 1, illustrates an eye, e.g. a first eye or a second eye.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several object of the hearing device system and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals or with a receiver/loudspeaker arranged close to or in the ear canal such as in a Behind-the-Ear type hearing aid or a Receiver-in-the Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A hearing device may be part of a "hearing system", which refers to a system comprising one or two hearing devices, disclosed in present description, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one object, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

It should be appreciated that reference throughout this specification to "one embodiment" or "an embodiment" or "an object" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various objects described herein. Various modifications to these objects will be readily apparent to those skilled in the art, and the generic principles defined herein may be applied to other objects.

The claims are not intended to be limited to the objects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follows.

The pupil size is a highly sensitive measure of the iris eye's width. Iris is a moving element of the eye, controlled by two muscles: constrictor and dilator. Both of the muscles have been found to have a correlation with Locus Coeruleus—part in the brain connected with reaction to stress in the human body. The specialized sympathetic nervous system (and thus Locus Coeruleus) is stimulated by the factors, such as increased stress, emotional change and cognitive functions such as memory retrieval, attention and language processing. Pupil dilation is caused by decreased activity of LC, which is called parasympathetic nervous system. FIG. 1 illustrates an eye (6A or 6B,), e.g. a first eye or a second eye, of a user in a 3-stage process of pupil dilation related to a cognitive task/listening effort. The pupil dilation is triggered by a mental task, which activates LC and the sympathetic nervous system. The pupil increases in size while performing the task. When the task is finished activation of LC decreases together with the size of the pupil. In FIG. 1 part I, the eye is in a standby mode, i.e. a first stage, where only external factors such as luminance or arousal influence the pupil size. In FIG. 1 part II, the eye is in an activation mode, i.e. a second stage, and the pupil size/dilation 20 has increased. The pupil dilation 20 is caused by given stimuli, such as speech, mental task, picture, problem requiring decision and/or a stressful situation. In FIG. 1 part III, the eye is back in a standby mode, i.e. a third stage, and the pupil size/dilation 20 has reduced. The pupil dilation presents the effect of nervous activation on the initial state, i.e. the first stage.

Pupillometry is a time dependent, objective and non-invasive measure of the fixated pupil size. In order to perform a pupillometry measurement and provide pupillary information (4A, 4B), a camera unit (160, 316, 318) configured to perform eye-tracking may be used. Pupillometry is a sensitive measure and there are factors such as light, eye blinking, head movements leading to the loss in data. The pupillary information (4A, 4B) may comprise a pupillary profile 21 which is a time series signal with frequency sampling from between 30 HZ to 120 Hz depending on the camera unit. It is usually tracked in short period of time within few milliseconds to few seconds per measurement generating the pupillary information (4A, 4B). Pupil size/dilation 20 varies from 0.5-9 mm. The pupillary profile 21 may be in a tonic mode—reflecting the overall activation of Locus Coreuleus. The pupillary profile 21 being in the tonic mode reflects a baseline measurement of eye generating a background pupillary information (18A, 18B) including the pupillary profile 21 in the tonic mode. The pupillary profile 21 may be in a phasic mode—reflects rapid changes in the pupil size 20 caused by dilator and is directly connected with the performed cognitive tasks/listening effort. Pupil size 20 in the phasic mode shows the increment up to 0.5 mm. The pupillary profile 21 in the phasic mode reflects an evaluation of the eye in response to a sound scene (5A, 5B)) generating the pupillary information (4A, 4B) including the pupillary profile 21 in the phasic mode.

Figure 2:
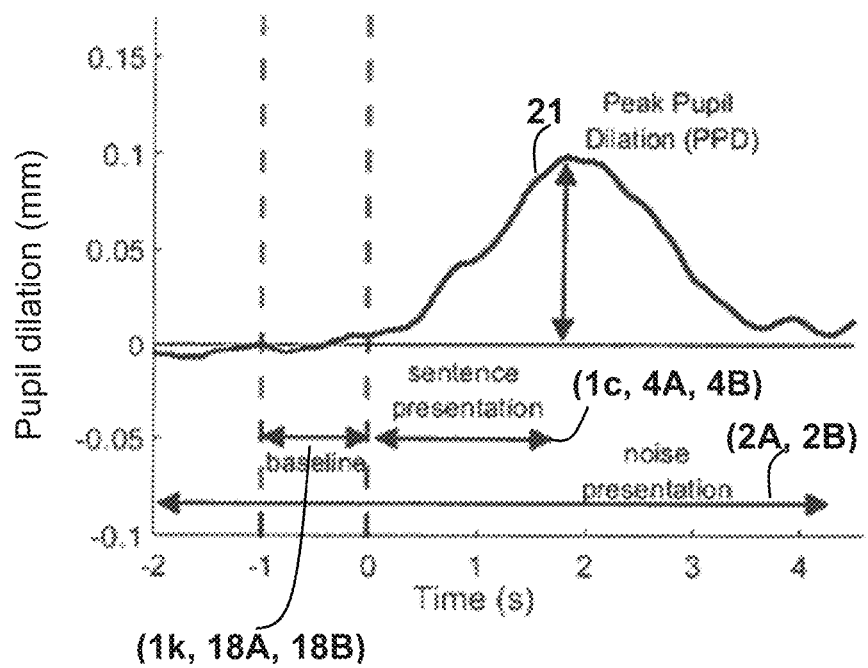
FIG. 2, illustrates a measured pupillary profile.

FIG. 2 illustrates a measured pupillary profile 21 of a user when being introduced to a background sound signal (2A, 2B) and/or a sound pattern (3A, 3B). The pupillary profile 21 is represented by a measure of the pupil dilation versus time in seconds. The user is introduced for the background sound signal (2A, 2B) during the complete evaluation/measurement of the pupillary profile 21, i.e. from −2 seconds to approximately 4.2 seconds. A baseline measurement 1K is performed from −1 seconds to 0 second generating a baseline pupillary information (18A, 18B). The user is then introduced to a sound scene (5A, 5B) comprising both the background sound signal (2A, 2B) and the sound pattern (3A, 3B) from 0 second to 1.8 seconds, wherein the eye (6A, 6B) of the user is evaluated 1C providing the pupillary information (4A, 4B) in response to the sound scene (5A, 5B). The baseline measurement 1k is not essential for the present disclosure.

Figure 3A:
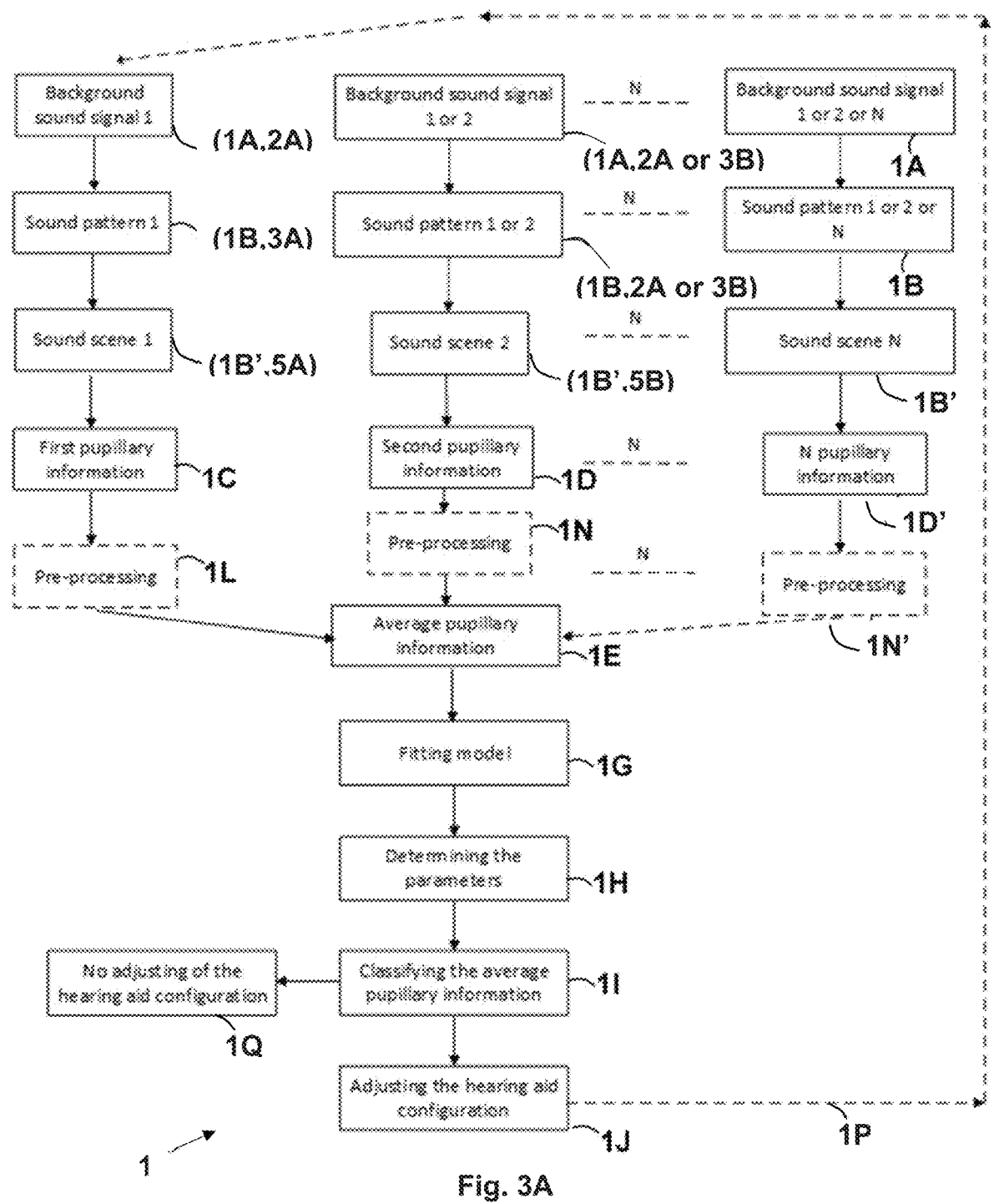
FIGS. 3A and 3B, illustrate the method for adjusting hearing aid configuration.
Figure 3B:
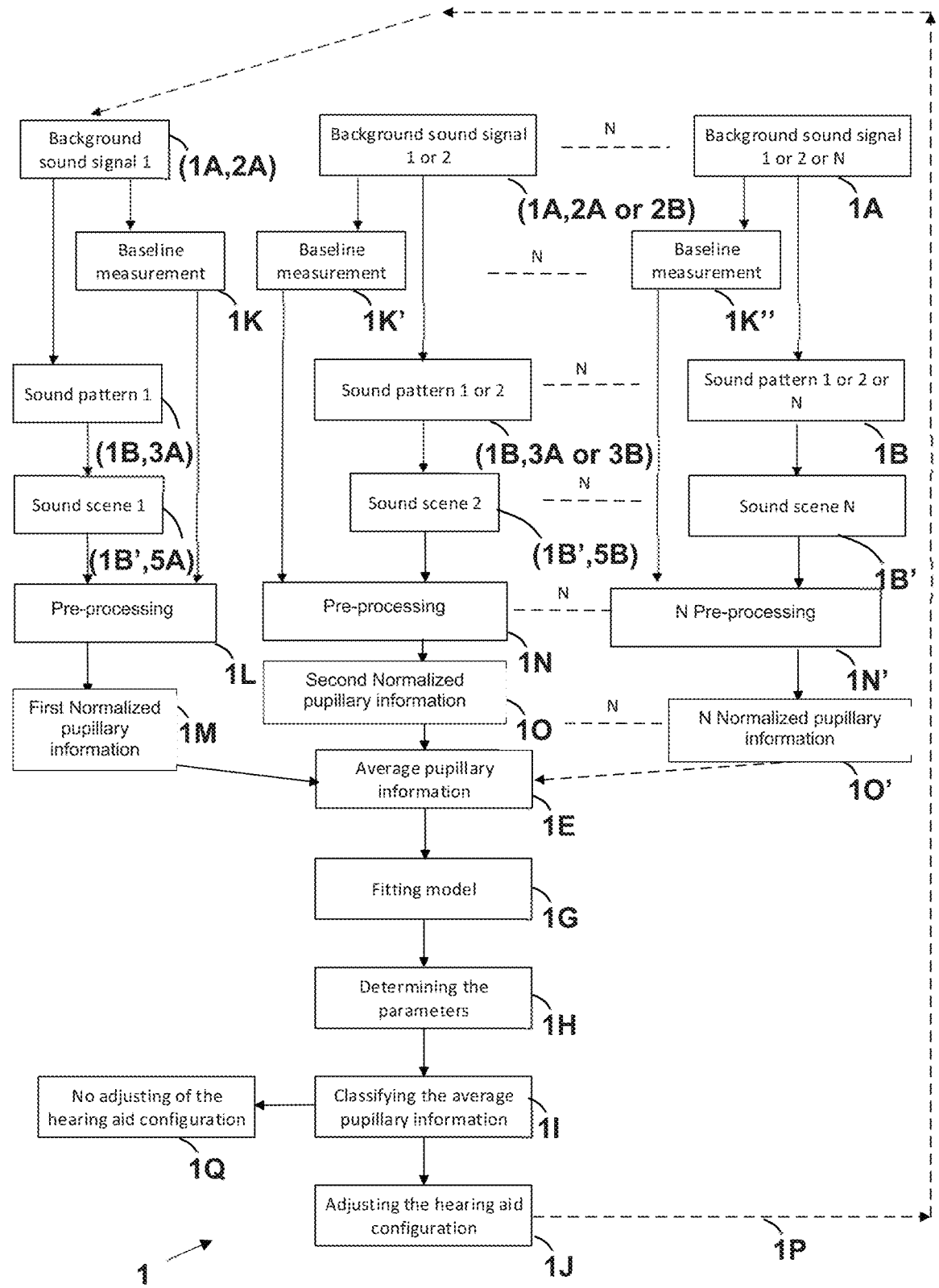

FIGS. 3A and 3B illustrate a method 1 for adjusting hearing aid configuration, where a user is wearing a hearing device (110/316).

In FIG. 3A, the method comprising transmitting 1A a first background sound signal 2A to the hearing device (160/316), transmitting 1B a first sound pattern 3A to the hearing device (110/316), wherein the first back ground sound signal 2A is combined/mixed 1B' with the first sound pattern 3A into a 1 first sound scene 5A. The method 1 further comprises evaluating 1C, via a camera unit (160/316/318), a first pupillary information 4A of a first eye 6A of the user in response to the first sound scene 5A comprising the first background sound signal 2A and the first sound pattern 3A, and wherein the evaluating 1C is repeated (1D, 1D') providing at least a second pupillary information 4B of the first eye 6A of the user in response to a second sound scene 5B being different from the first sound scene 5B, and where an averaged pupillary information 22 is provided 1E based on an average between the first pupillary information 4A and at least the second pupillary information 4B. Additionally, the method 1 comprises selecting 1G a pupillary fitting model 10 based on the averaged pupillary information, determining 1H a first parameter 11A and at least a second parameter 11B of the pupillary fitting model 10 based on the averaged pupillary information 22. The averaged pupillary information 22 may then be classified 1I into either a first category 12A or at least a second category 12B based on the first parameter 11A and the at least second parameter 11B, and wherein the hearing aid configuration is adjusted 1J if the averaged pupillary information is in the first category 12A, and the hearing aid configuration is not adjusted 1Q if the averaged pupillary information is in the second category 12B.

After adjusting the hearing aid configuration, the method 1 may be repeated 1P for the new hearing aid configuration.

The transmitting (1A, 1B) of background sound signals (2A,2B,2) and sound pattern (3A,3B,3) to be combined 1B' in sound scenes (5A,5B,5) and the evaluation of pupillary information (4A,4B,4) may be repeated N times.

Optionally, the method 1 may comprise pre-processing 1L of the first pupillary information 4A for removing artifacts in the first pupillary information 4A and the first baseline pupillary information 18A. The pre-processing may comprise detecting eye-blinks in the pupillary information (4A, 4B), where the pupillary information (4A, 4B) comprises data of pupil size of the first eye 6A, and the eye-blinks are detected as a value of the pupil size being below a pupil size threshold. Furthermore, the pre-processing 1L may comprise removing the pupil sizes being below the pupil size threshold from the pupillary information (4A, 4B), and interpolating the remaining pupil size.

Additionally, the pre-processing 1L may comprise alignment in time the sound scenes (5A, 5B) by interpolating a time length of each of the sound scene (5A, 5B) onto a reference time vector in order to remove any differences in the time length of each of the sound scene (5A, 5B), and filtering the sound scenes (5A,5B) being aligned in time for removing high frequency artifacts from the sound scenes (5A,5B).

The pre-processing may be repeated (1N, 1N') N times with different sound scenes (5A, 5B), such as the first sound scene 5A and the second sound scene 5B, and where N is determined based on a quality of the evaluation of the pupillary information (4A, 4B), such as the first pupillary information 4A and/or the second pupillary information 4B or other pupillary information in response to a sound scene.

In 3B, the method 1 comprising performing a first baseline measurement 1K, via the camera unit (160/316/318), which includes a measurement of a first baseline pupillary information 18A of the first eye 6A of the user in response to the first background sound signal 2A. The method may further comprise the pre-processing 1L the first pupillary information 4A and the first baseline pupillary information 18A for removing artifacts in the first pupillary information 4A and the first baseline pupillary information 18A, and providing a normalized first pupillary information 19A based on normalization 1M of the first pupillary information 4A with the first baseline pupillary information 18A, and wherein the pre-processing is repeated (1N,1N') of at least the second pupillary information 4B in response to the second sound scene 5B and of at least a second baseline pupillary information 18B, wherein the second baseline pupillary information 18B is provided in response to a second background sound signal 2B and a second baseline measurement 1K', and wherein a normalized second pupillary information 19B is provided based on a normalization 1O of the second pupillary information 4B with the second baseline pupillary information 18B, and wherein the averaged pupillary information 22 is provided 1E based on an average between the normalized first pupillary information 19A and at least the normalized second pupillary information 19B.

The pre-processing may be repeated (1N, 1N') N times with different sound scenes (5A, 5B), such as the first sound scene 5A and the second sound scene 5B, and where N is determined based on a quality of the evaluation of the pupillary information (4A, 4B), such as the first pupillary information 4A and/or the second pupillary information 4B or other pupillary information in response to a sound scene. Furthermore, the normalization may be repeated N times, and the averaging into the averaged pupillary information 22 may comprises N times of normalized pupillary information.

Alternatively, the normalization may be repeated N times, and the averaging into the averaged pupillary information 22 may comprises a plurality of normalized pupillary information wherein the number of normalized pupillary information (19A,19B,19) may be determined by the quality of each normalized pupillary information (19A,19B,19) or pre-determined.

The transmitting (1A, 1B) of background sound signals (2A,2B,2) and sound pattern (3A,3B,3) to be combined 1B' in sound scenes (5A,5B,5) and the evaluation of pupillary information (4A,4B,4) may be repeated N times.

After adjusting the hearing aid configuration, the method 1 may be repeated 1P for the new hearing aid configuration.

Figure 4:
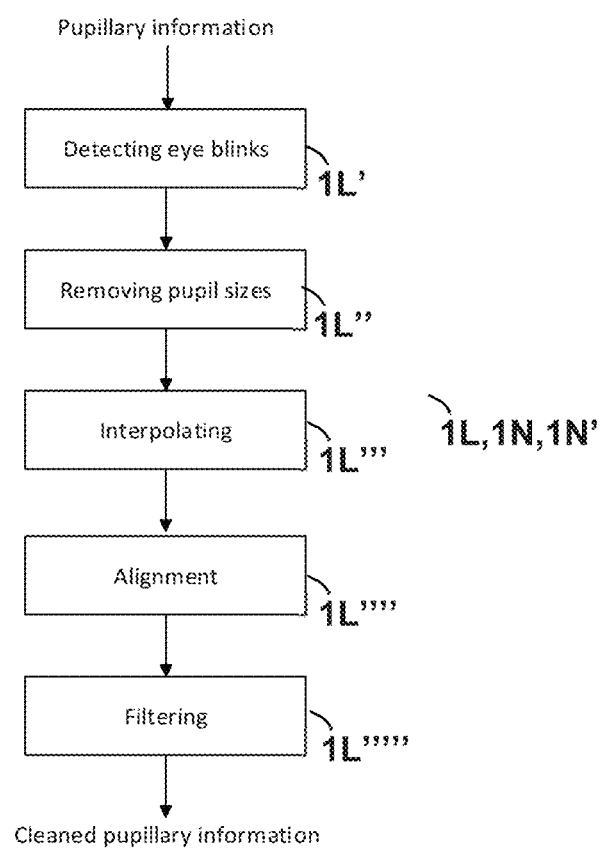
FIG. 4, illustrates the pre-processing.

FIG. 4 illustrates the pre-processing (1L,1N,1N') comprising detecting 1L' eye-blinks in the pupillary information (4,4A,4B) and in the baseline pupillary information (18, 18A,18B), where the pupillary information (4,4A,4B) and the baseline pupillary information (18,18A,18B) comprises data of pupil size of the first eye 6A, and the eye-blinks are detected as a value of the pupil size being below a pupil size threshold, removing 1L" the pupil sizes being below the pupil size threshold from the pupillary information (4,4A, 4B) and the baseline pupillary information(18,18A,18B), and interpolating 1L''' the remaining pupil size. The pre-processing 1L may further comprise alignment 1L'''' in time the sound scenes (5,5A,5B) by interpolating a time length of each of the sound scene (5,5A,5B) onto a reference time vector in order to remove any differences in the time length of each of the sound scene (5,5A,5B), and filtering 1L''''' the sound scenes (5,5A,5B) being aligned in time for removing high frequency artifacts from the sound scenes (5,5A,5B).

FIGS. 5A, 5B and 5C illustrate the sound pattern (3,3A, 3B), the background sound signals (2,2A,2B) and the sound scene (5,5A,5B) respectively.

In FIG. 5A, the sound pattern is illustrated comprising a speech sample 13 or a speech corpus 13 having a linguistic complexity 15, sentence length 14 and a first sound level 16A.

In FIG. 5B, the background sound signals (2,2A,2B) is illustrated comprising a background sample 17 including a tone, a sound or a speech sample. The background sample 17 may have a sample length 14 and a second sound level 16B.

In FIG. 5C, the sound scene (5,5A,5B) is illustrated comprising the sound pattern (3,3A,3B) and the background sound signals (2,2A,2B). The first sound level 16A may be different from the second sound level 16B. By adjusting the ratio between the first sound level 16A and the second sound level 16B may result in a change in a speech recognition of the speech sample 13 in the sound pattern (3,3A,3B).

Figure 6A:
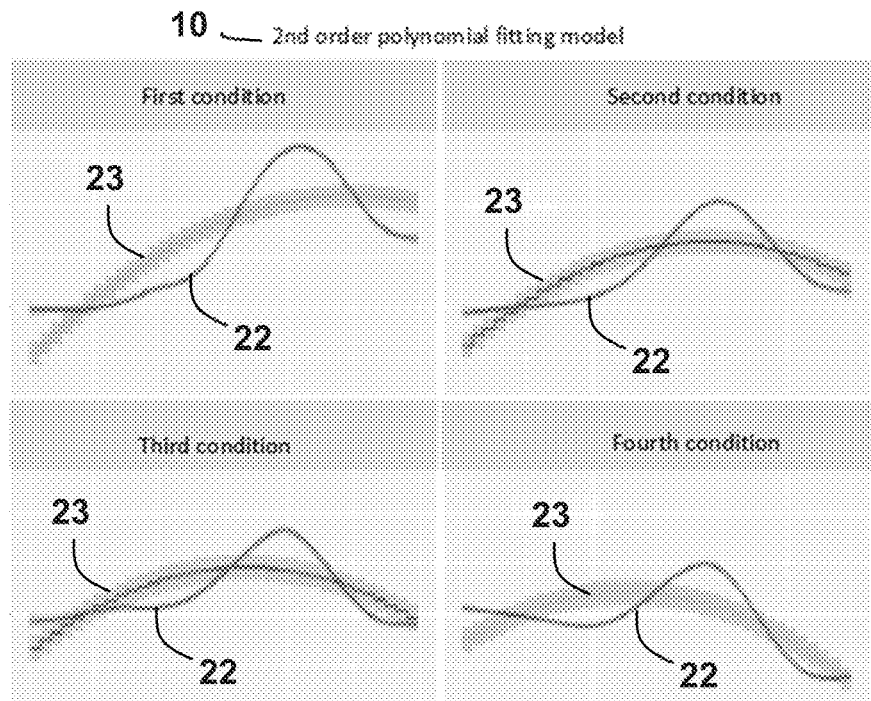
FIGS. 6A, 6B and 6C, illustrate a selection of different pupillary fitting model.
Figure 6B:
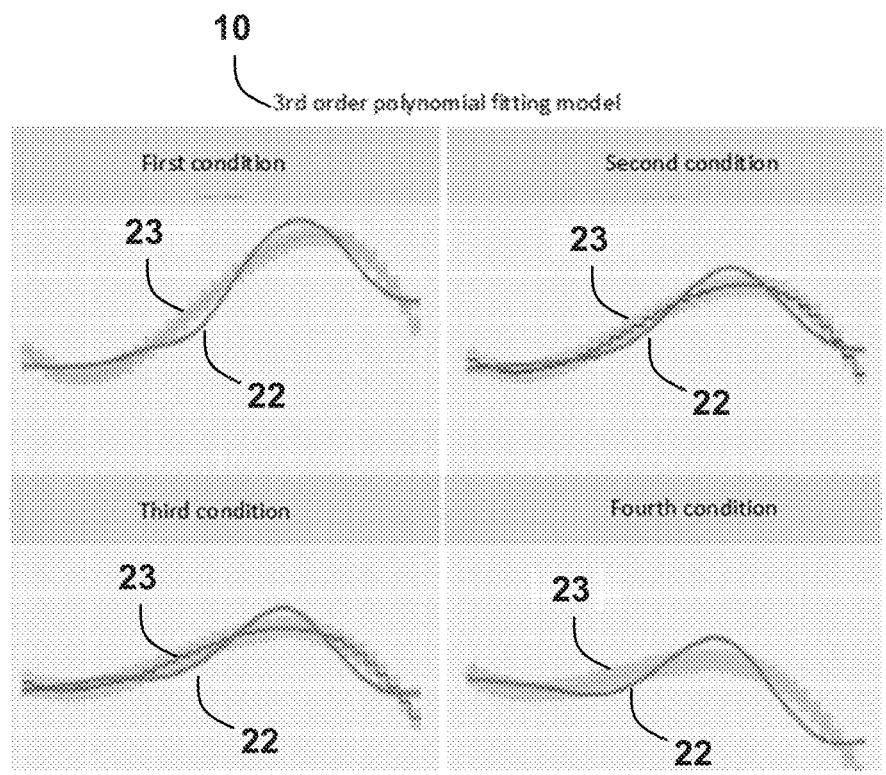
Figure 6C:
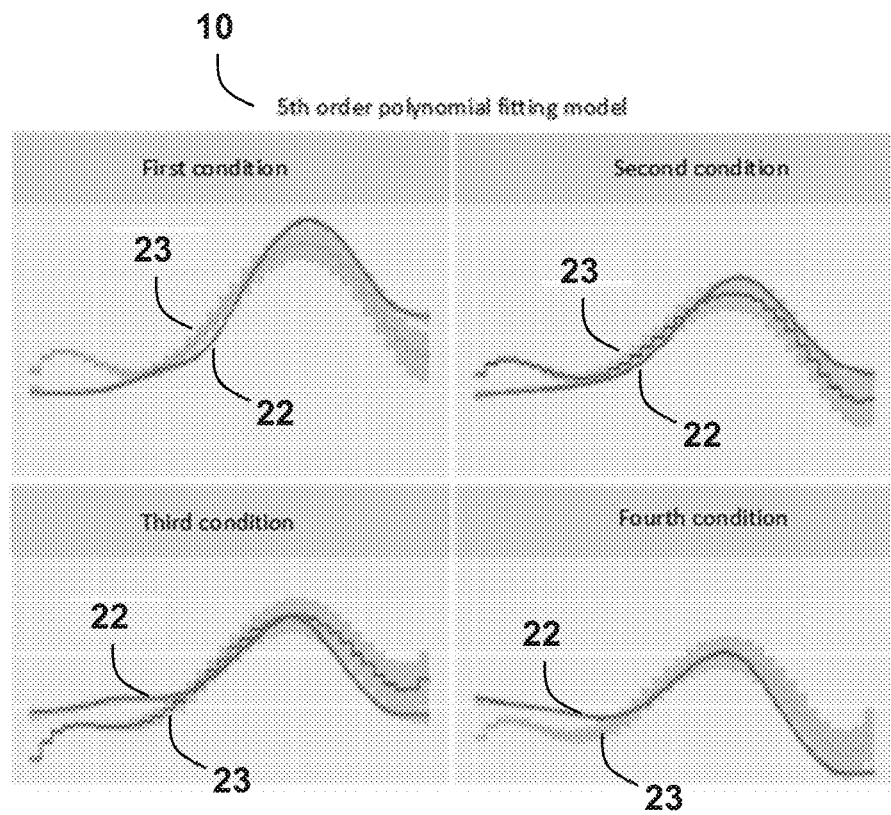

FIGS. 6A, 6B and 6C illustrates a selection of different pupillary fitting models 10, where for each pupillary fitting model 10 a fitting curve 23 is generated in order to construct a theoretical estimation of the averaged pupillary information 22 in four different conditions of the sound scenes (5,5A,5B) being used for providing the averaged pupillary information 22.

In the first condition, the sound scenes (5,5A,5B) being used in order to determine the averaged pupillary information 22 may comprise a sound pattern (3,3A,3B) together with a background sound signal (2,2A,2B) which provides a speech recognition threshold (SRT) of 50% accuracy of the sound pattern (3,3A,3B). No noise cancelling is taking place in the hearing device.

In the second condition, the speech recognition threshold is set to 95% accuracy of the sound pattern (3,3A,3B). No noise cancelling is taking place in the hearing device. In the third condition, the speech recognition threshold is set to 50% accuracy of the sound pattern (3,3A,3B). Noise cancelling is taking place in the hearing device.

In the fourth condition, the speech recognition threshold is set to 95% accuracy of the sound pattern (3,3A,3B). Noise cancelling is taking place in the hearing device.

Changing the SRT may be provided by increasing/decreasing the second sound level 16B (i.e. sound level of the background sound signal (2,2A,2B)) and/or decreasing/increasing the first sound level 16A (i.e. the sound level of the sound pattern (3,3A,3B). In order to increase SRT, can be done by decreasing the second sound level 16B and/or increasing the first sound level 16A.

In FIG. 6A, the pupillary fitting model 10 is a second order polynomial fitting model.

In FIG. 6B, the pupillary fitting model 10 is a third order polynomial fitting model.

In FIG. 6C, the pupillary fitting model 10 is a fifth order polynomial fitting model.

Figure 7:
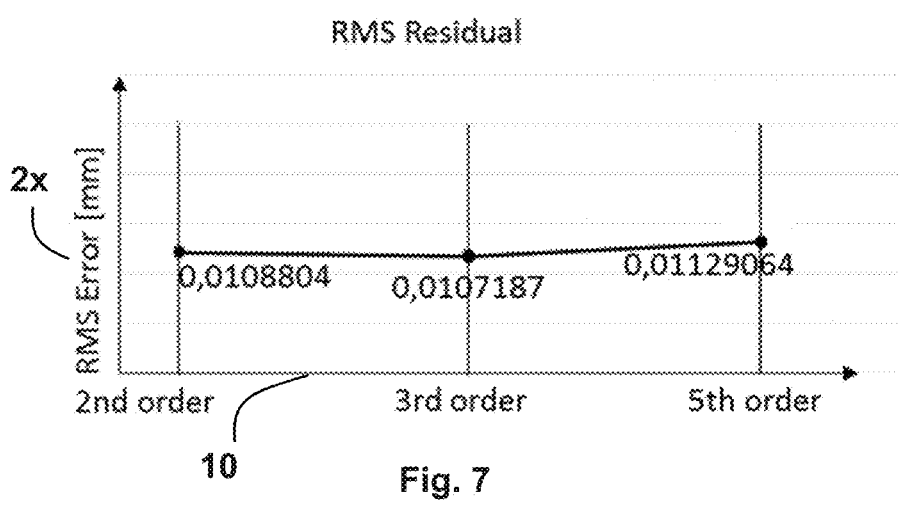
FIG. 7, illustrates a Root-mean squared residual analysis of each fitting.

In FIG. 7, a Root-mean-squared residual analysis is provided on each fitting described in FIGS. 6A, 6B and 6C. A low Root-mean-squared residual 2x indicates that the selected pupillary fitting model 10 has generated a fitting curve 23 which provide a good theoretical estimation of the averaged pupillary information 22, however, a high Root-mean-squared residual indicates that the fitting curve 23 provides a poor theoretical estimation of the average pupillary information 22. Between the second order, the third order and the fifth order polynomial fitting model, the third order polynomial fitting model provides the fitting curve 23 which represents best the averaged pupillary information 22.

Figure 8A:
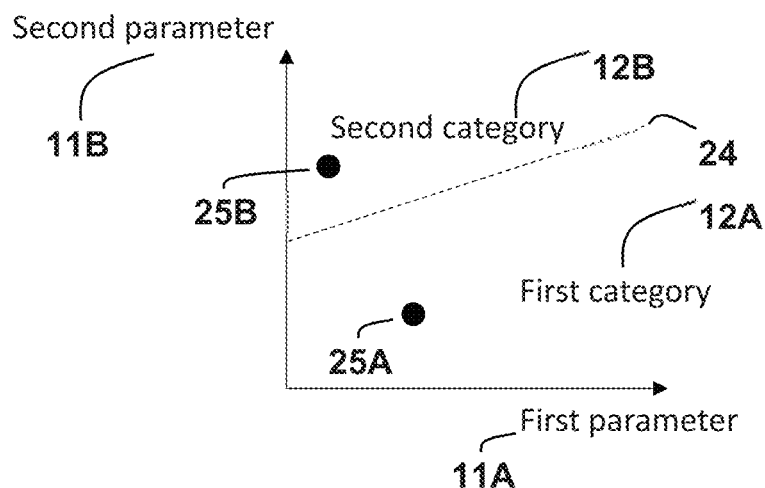
FIGS. 8A-8B, illustrate an example on how to define the first category and the second category.
Figure 8B:
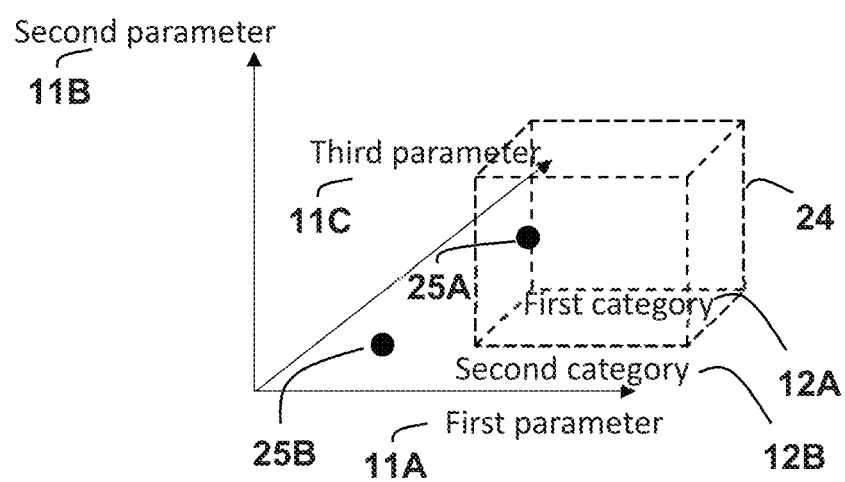

The first parameter 11A and the second parameter 11B may be provided by the pupillary fitting model 10. The parameters (11A, 11B) may be the variables included by the pupillary fitting model 10. FIGS. 8A and 8B illustrate examples on how to define the first category 12A and the second category 12B in relation to the parameters (11A, 11B). In FIG. 8A, the first category 12A is separated from the second category via a category threshold 24. The category threshold 24 may be determined by the pupillary fitting model 10 or the sound scene. In this example, the category threshold 24 is linear. The relation between the first parameter 11A and the second parameter 11B is illustrated by the points 25A and 25B. At point 25A the relation between the first parameter 11A and the second parameter 11B results in that the averaged pupillary information 22 is classified into the first category 12A. At point 25B the averaged pupillary information 22 is classified into the second category 12B. In FIG. 8B, the classification of the averaged pupillary information 22 is based on the first parameter 11A, the second parameter 11B and a third parameter 11C. This example may correspond to a pupillary fitting model 10 being a second order polynomial fitting model. The category threshold 24 is defined as a 3-dimensional form, in this example a square shaped category threshold 24. At point 25A, the relation between the first parameter 11A, the second parameter 11B and the third parameter 11C results in that the averaged pupillary information 22 is classified into the first category 12A. At point 25B the averaged pupillary information 22 is classified into the second category 12B.

FIGS. 9A to 9D illustrate different example of a hearing device system 100 for adjusting hearing aid configuration. The hearing device system 100 comprising the hearing device 110 configured to receive the first background sound signal 2A, and where the hearing device 110 receives the first sound pattern 3A. Additionally, the hearing device system 100 comprises the camera unit 160 configured to evaluate the first eye 6A of the user 120 in response to a first sound scene 5A comprising the first background sound signal 2A and the first sound pattern 3A and providing a first pupillary information 4A based on the first sound scene 5A. The camera unit 160 is further configured to repeat the evaluation of the first eye 6A and provide at least a second pupillary information 4B of the first eye 6A in response to a second sound scene 5B being different from the first sound scene 5A. Additionally, the hearing device system 100 comprises a processing unit 112 configured to provide the averaged pupillary information 22 based on an average between the first pupillary information 4A and at least the second pupillary information 4B. The hearing device system 100 comprises a fitting model unit 114 configured to select a pupillary fitting model 10 based on the averaged pupillary information 22, and the fitting model 10 is further configured to determine a first parameter 11A and at least a second parameter 11B of the pupillary fitting model 10 based on the averaged pupillary information 22. The hearing device system further comprises a classifier unit 116 configured to classify the averaged pupillary information 22 into either a first category 12A or at least a second category 12B based on the first parameter 11A and the at least second parameter 11B, and wherein the hearing aid configuration is adjusted if the averaged pupillary information 22 is in the first category 12A, and the hearing aid configuration is not adjusted if the averaged pupillary information 22 is in the at least second category 12B.

Figure 9A:
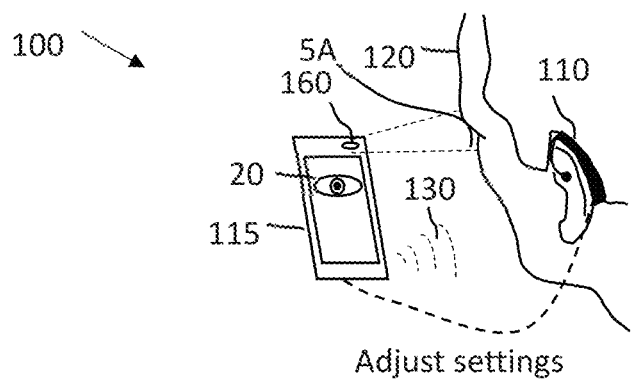
FIGS. 9A to 9D, illustrate different example of a hearing device system.

In FIG. 9A, the hearing device system 100 comprises a smartphone 115 and the hearing device 110 is a hearing aid 110. In this specific example, the hearing aid 110 is a Behind-The-Ear hearing aid, however, other types of hearing aid may be used instead, e.g. a cochlear implant hearing aid, an In-The-Ear hearing aid etc. The camera unit 160 is built into the smartphone 115. The processing unit 112, and/or the fitting model 114, and/or the classification unit 116 may be built into the smartphone, a server configured to be wireless connected to the smartphone, or the hearing device 110. The smartphone 115 may be configured to receive the sound scene (5,5A,5B) from a server and transmit the sound scene (5,5A,5B) to the hearing device 110. The camera unit 160 is then evaluating the pupillary information (4,4A,4B) of the user 120 in response to the sound scenes (5,5A,5B). The sound scenes (5,5A,5B) may be transmitted to the hearing device 120 via a wireless communication link 130, such as Bluetooth link or an inductive link, or the sound scenes (5,5A,5B) may be transmitted acoustically 130 via a speaker in the smartphone 115 to a microphone of the hearing device. Alternatively, the sound scenes (5,5A,5B) may be transmitted to the hearing device 110 via a wired connection between the smartphone 115 and the hearing device 110. The camera unit 160 evaluates then the pupil size/pupil dilation 20 in response to the sound scenes (5,5A,5B). The smartphone 115 or the server may perform one or more of following features, namely; the selecting of the pupillary fitting model 10, classification of the averaged pupillary information 22 into the first category 12A or the second category 12B and the determine of the adjustment of the hearing aid configuration. The hearing aid configuration in this example is confined to hearing aid settings. When the adjustment of the hearing aid setting is determined, then the smartphone is configured to transmit the adjust settings to the hearing device 110, i.e. the hearing aid 110.

Figure 9B:
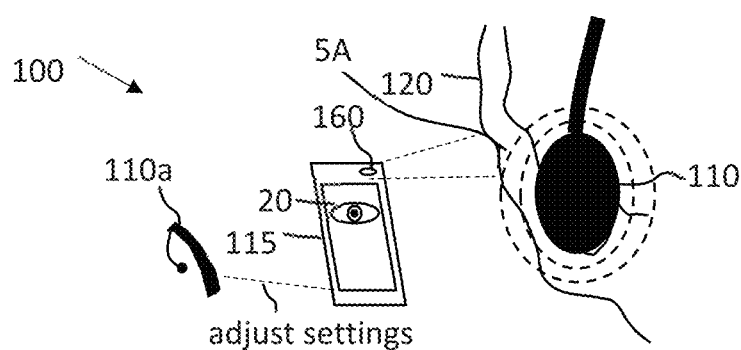

In FIG. 9B, the hearing device 110 is a headphone 110, and the hearing aid 110a is not worn by the user during the processing of the method 1, however, the smartphone is still configured to transmit the adjust settings, i.e. the hearing aid configuration, to the hearing aid 110a.

Figure 9C:
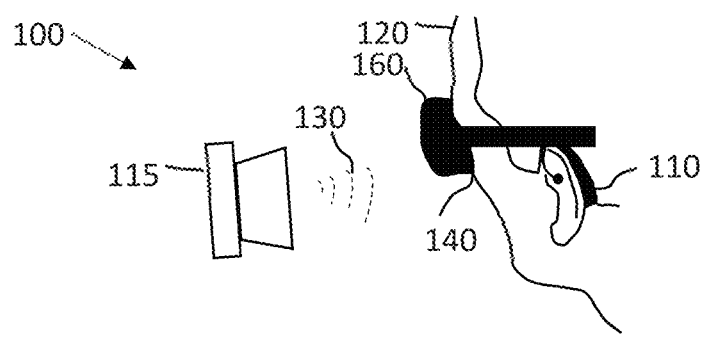

In FIG. 9C, the smartphone is replaced by a speaker 115 configured to communicate with a server or a smartphone in order to receive the sound scenes (5,5A,5B) and output acoustically 130 the sound scenes (5,5A,5B) to the user 120. The camera unit 160 is implemented into an eye-tracker device, such as a goggle. The hearing device 110 is a hearing aid 110, wherein the hearing aid 110 is configured to receive acoustically 130 the sound scene (5,5A,5B) via a microphone within the hearing aid 110. The pupillary information (4,4A,4B) may be transmitted wirelessly from the eye-tracking device to the smartphone or the server, and either the smartphone or the server may perform one or more of following features, namely; the selecting of the pupillary fitting model 10, classification of the averaged pupillary information 22 into the first category 12A or the second category 12B and the determine of the adjustment of the hearing aid configuration.

Figure 9D:
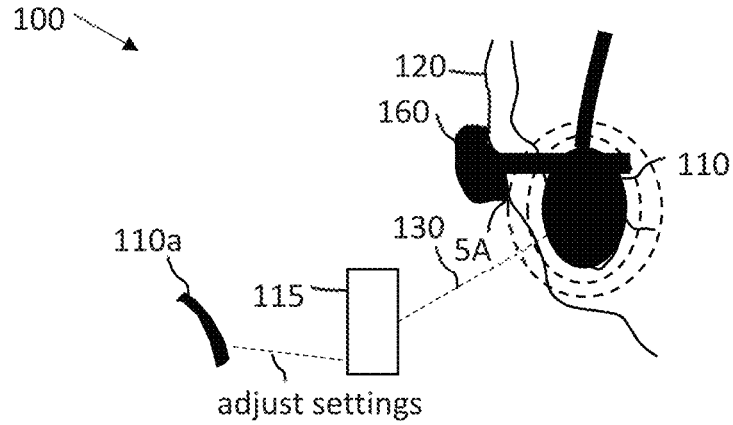

In FIG. 9D, the speaker 115 is replaced with a smartphone 115. The hearing device 110 may be a headphone 110, and the camera unit 160 may be built into an eye-tracking device, such as a goggle. The performing of one or more of following features, namely; the selecting of the pupillary fitting model 10, classification of the averaged pupillary information 22 into the first category 12A or the second category 12B and the determine of the adjustment of the hearing aid configuration, and the communication between the hearing aid 110a, the smartphone 115, the camera unit 160 and the hearing device 110 is described in FIGS. 9A to 9C.

The smartphone or the speaker may be denoted as an external streaming device.

The server may be an icloud server or a computer.

Figure 10A:
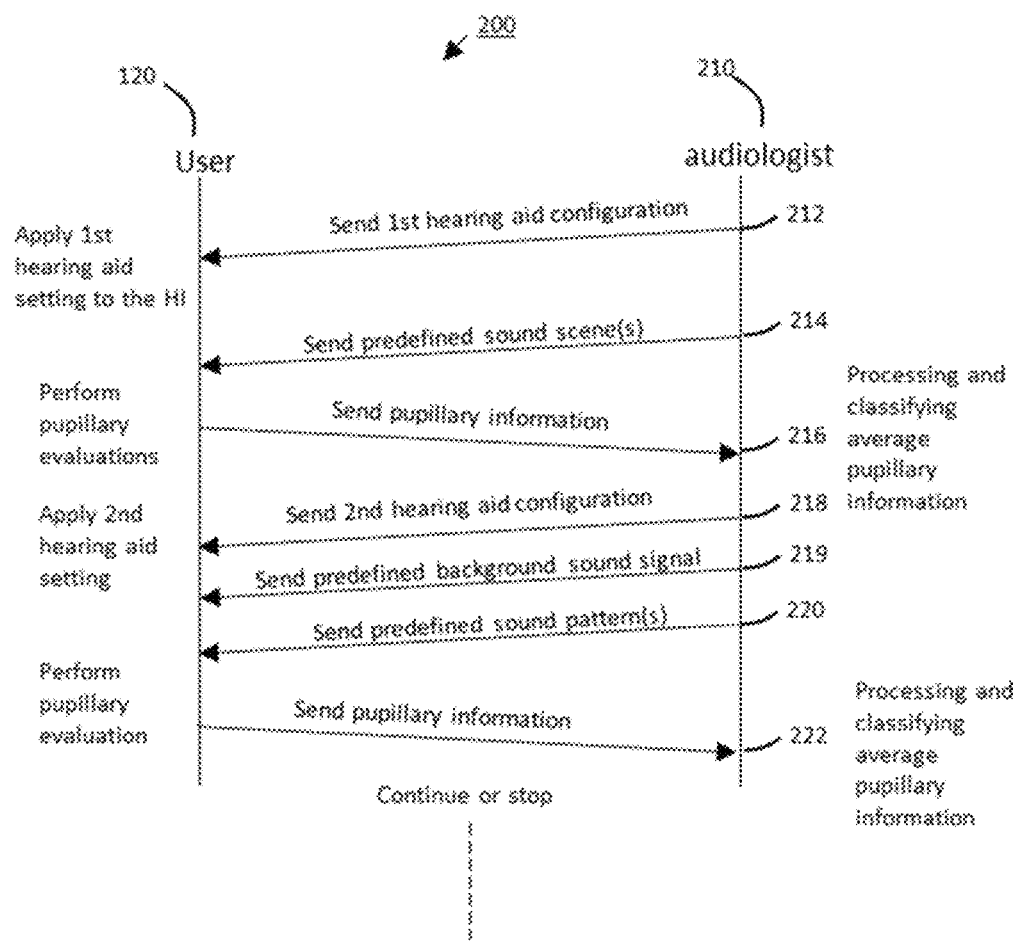
FIGS. 10A and 10B illustrate different examples of implementations of the method.
Figure 10B:
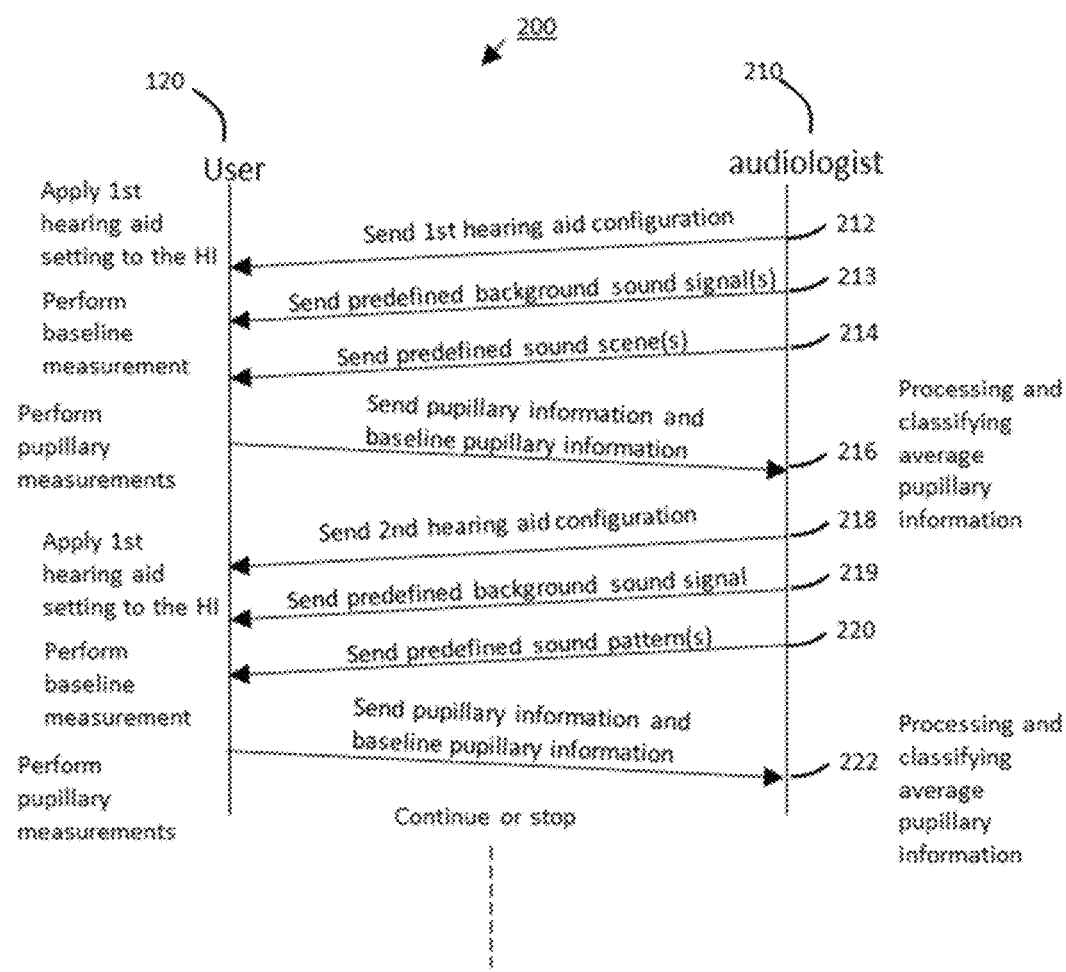

FIGS. 10A and 10B illustrate different examples of implementations of the method 1 and the hearing device system 100 where the adjustment of the hearing aid configuration, e.g. the fitting of the hearing aid setting of a hearing aid 110, may be done remotely or none-remotely. Remotely adjustment or fitting is defined as an adjustment or fitting of the hearing aid where the sound pattern and the adjustment or fitting the hearing aid configuration are communicated via a cloud based server and/or via a long distance communication network, such as telephone network, internet, WIFI etc.

The skilled person having benefit from the present disclosure will appreciate that the pro-posed concepts can lend itself to remote fitting concepts, where an audiologist can be at a different, remote location or does not even have to be involved at all. FIG. 2a schematically illustrates an example sequence chart 200 for remotely fitting the hearing aid 110.

In FIG. 10A, as a first act, a hearing impaired user 120 receives a message 212 from a remote site 210 to apply first hearing aid settings, i.e. the hearing aid configuration. The message 212 can for example be received by an external streaming device 115 associated with the user 120, such as a user's smartphone or the hearing aid 110 itself. Message 212 can comprise instructions to apply first hearing aid settings stored at the user side, for example stored in the user's smartphone 115 or hearing aid 110, or the message 202 itself could contain the first hearing aid settings. The remote site 210 could be a computer/server of a remote audiology lab controlled by an audiologist, for example. The remote site and the user 120 could be connected via internet, for example. For this purpose, an external streaming device 115, such as a smartphone, computer, or a virtual reality headset, could be associated with the hearing impaired user 120. The external streaming device 115 can then adjust the current hearing aid settings in accordance with the first hearing aid settings. This can be done via a wired or wireless communication link between the user device and the hearing aid 110, for example.

Then, after having applied the first hearing aid settings to the user's hearing aid 110, the external streaming device 115 can be instructed via a message 214 to playback one or more predefined sound scenes (5,5A,5B). The playback could be done via a smartphone, a laptop or desktop computer, or the like. Message 214 could comprise instructions to playback one or more predefined sound scenes (5,5A,5B) stored at the user side, or the message 202 itself could contain one or more predefined digital sound scenes (5,5A,5B).

Pupillometric measurements (e.g. measurement of the pupil dilation, i.e. the evaluation of the first eye/second eye) are then performed at the user side in order evaluate the user's cognitive load for listening to and identifying the one or more predefined sound scenes (5,5A,5B) with the first hearing aid settings. The pupillometric measurements provides the pupillary information (4,4A,4B). As mentioned above, the pupillometric measurements can be performed using an eye tracker or pupilometer 160, which can be integrated into a smartphone, a PC, a tablet, or a virtual reality headset worn by the user 120, for example. The pupillary information (4,4A,4B) may then be pre-processed 1L and the average pupillary information 22 may then be determined and the classification of the average pupillary information 22 may then be performed 216.

Next, the hearing impaired user 120 can receive a further message 218 from the remote site 210 to apply different second hearing aid settings. The current hearing aid settings can then be adjusted according to the second hearing aid settings. After having applied the second hearing aid settings, the user device can be instructed via a message 220 to playback the one or more predefined sound scenes (5,5A, 5B). Pupillometric measurements are then performed again in order to measure the user's cognitive load for listening to and identifying the one or more predefined sound scenes (5,5A,5B) with the second hearing aid settings. The second pupillary information 4B provided by the pupillometric measurements for the second hearing aid settings can then be send back to the remote 210 site via message 222.

This procedure can be repeated multiple times for different potential hearing aid settings. After pupillometric measurement results for all potential hearing aid settings have been collected, the remote site 210 can evaluate the pupillometric measurement results and select the optimum hearing aid settings which have led to the pupillometric measurement results indicating the least cognitive load for listening to and identifying the one or more predefined sound scenes. These optimum hearing aid settings can then be applied.

FIG. 10B illustrates a similar example as illustrated in FIG. 10A, however, the user receives 213,214 both background sound signals (2,2A,2B) and the sound scenes (5,5A, 5B). Baseline pupillary measurements are then performed in order to measure the user's cognitive load to the background sound signals (2,2A,2B) resulting in baseline pupillary information (18,18A,18B), and thereafter, pupillometric measurement may then be performed in order to measure the user's pupillary information (4,4A,4B) in response to the one or more predefined sound scenes (5,5A,5B) with a first hearing aid configuration, i.e. the hearing aid settings, transmitted 212 from the remote site 210. Both the baseline pupillary information (18,18A,18B) and the pupillary information (4,4A,4B) are transmitted 216 to the remote site 210. The pupillary information (4,4A,4B) and the baseline pupillary information (4,4A,4B) may then be pre-processed 1L, and the pupillary information (4,4A,4B) may then be normalized with the baseline pupillary information. The average pupillary information 22 may then be determined by the normalized pupillary information, and the classification of the average pupillary information 22 may then be performed 216. Steps 212 to 216 are then repeated in steps 218 to 222 with a second hearing aid configuration. The steps may be repeated numerous times.

The communication between the remote site 210 and the user may be provided via a long range communication protocol and a short range communication. A server may be involved in the communication between the remote site 210 and the user 120. The long range communication protocol may for example be a telephone network, such as 3G, 4G 5G etc., and the short range communication protocol may for example be Bluetooth protocol, Bluetooth Low energy, or an inductive link. The server may be an iCloud server.

The invention claimed is:

1. A method for adjusting hearing aid configuration, where a user is wearing a hearing device, the method comprising;

transmitting a first background sound signal to the hearing device, transmitting a first sound pattern to the hearing device, evaluating, via a camera unit, a first pupillary information of a first eye of the user in response to a first sound scene comprising the first background sound signal and the first sound pattern, and wherein the evaluating is repeated providing at least a second pupillary information of the first eye of the user in response to a second sound scene being different from the first sound scene, and where an averaged pupillary information is provided based on an average between the first pupillary information and at least the second pupillary information, and selecting a pupillary fitting model based on the averaged pupillary information, determining a first parameter and at least a second parameter of the pupillary fitting model based on the averaged pupillary information, classifying the averaged pupillary information into either a first category or at least a second category based on the first parameter and the at least second parameter, and wherein the hearing aid configuration is adjusted if the averaged pupillary information is in the first category, and the hearing aid configuration is not adjusted if the averaged pupillary information is in the second category.

2. A method according to claim 1, wherein the second sound scene comprises a combination of a second background sound signal received by the hearing device and the first sound pattern or a combination of a second sound pattern received by the hearing device and the first background sound signal, or a combination of the first background sound signal and the second sound pattern.

3. A method according to claim 2, wherein sound patterns, such as the first sound pattern and the second sound pattern, comprise a speech sample with a sample length in time, a linguistic complexity and/or a sound level.

4. A method according to claim 2, wherein the first background sound signal and the second background sound signal comprise a background sample configured with a sample length in time, and/or a sound level, and wherein the background sample comprises a background speech sample, a tone signal, a synthesized acoustic signal, and/or an acoustical environment sound.

5. A method according to claim 1, wherein the adjusting of the hearing aid configuration is based on the first parameter and the at least second parameter of the fitting model or based on a relation between the first parameter and the at least second parameter.

6. A method according to claim 1, wherein the method comprising;

performing a first baseline measurement, via the camera unit, which includes a measurement of a first baseline pupillary information of the first eye of the user in response to the first background sound signal, pre-processing the first pupillary information and the first baseline pupillary information for removing artifacts in the first pupillary information and the first baseline pupillary information, and providing a normalized first pupillary information based on normalization of the first pupillary information with the first baseline pupillary information, and wherein the pre-processing is repeated of at least the second pupillary information in response to the second sound scene and of at least a second baseline pupillary information, wherein the second baseline pupillary information is provided in response to a second background sound signal and a second baseline measurement, and wherein a normalized second pupillary information is provided based on a normalization of the second pupillary information with the second baseline pupillary information, and wherein the averaged pupillary information is provided based on an average between the normalized first pupillary information and at least the normalized second pupillary information.

7. A method according to claim 6, wherein the pre-processing is comprising;

detecting eye-blinks in the pupillary information and in the baseline pupillary information, where the pupillary information and the baseline pupillary information comprises data of pupil size of the first eye, and the eye-blinks are detected as a value of the pupil size being below a pupil size threshold, removing the pupil sizes being below the pupil size threshold from the pupillary information and the baseline pupillary information, and interpolating the remaining pupil size.

8. A method according to claim 6, wherein the pre-processing is comprising;

alignment in time the sound scenes by interpolating a time length of each of the sound scene onto a reference time vector in order to remove any differences in the time length of each of the sound scene, and filtering the sound scenes being aligned in time for removing high frequency artifacts from the sound scenes.

9. A method according to claim 1, wherein the hearing aid configuration includes hearing aid settings, optimal mapping parameters of stimulation electrodes connected to a cochlear implant where the hearing device is a cochlear implant, placement of an ear piece of the hearing device into an ear canal and/or frequency response of the hearing device.

10. A method according to claim 1, wherein the hearing device, is a headphone, a goggle comprising a speaker, a smartphone, a headset, a speaker, a hearing aid, or a cochlear implant.

11. A method according to claim 1, wherein the pupil information comprises information about pupil dilation and/or pupil size.

12. A method according to claim 1, wherein the evaluation and/or the pre-processing are repeated N times with different sound scenes, such as the first sound scene and the second sound scene, and where N is determined based on a quality of the evaluation of the pupillary information, such as the first pupillary information and/or the second pupillary information or other pupillary information in response to a sound scene.

13. A method according to claim 1, wherein the measure of the first baseline measurement and the measure of the second baseline measurement and the evaluating of the pupillary information in response to a sound scene is performed on the first eye and a second eye of the user.

14. A hearing device system for adjusting hearing aid configuration, the hearing device system comprising;

a hearing device configured to receive a first background sound signal, and where the hearing device receives a first sound pattern, a camera unit configured to evaluate a first eye of the user in response to a first sound scene comprising the first background sound signal and the first sound pattern and providing a first pupillary information based on the first sound scene, and wherein the camera unit is further configured to repeat the evaluation of the first eye of the user and provide at least a second pupillary information of the first eye of the user in response to a second sound scene being different from the first sound scene, a processing unit configured to provide an averaged pupillary information based on an average between the first pupillary information and at least the second pupillary information, a fitting model unit configured to select a pupillary fitting model based on the averaged pupillary information, and the fitting model is further configured to determine a first parameter and at least a second parameter of the pupillary fitting model based on the averaged pupillary information, a classifier unit configured to classify the averaged pupillary information into either a first category or at least a second category based on the first parameter and the at least second parameter, and wherein the hearing aid configuration is adjusted if the averaged pupillary information is in the first category, and the hearing aid configuration is not adjusted if the averaged pupillary information is in the at least second category.

15. A hearing device system according to claim 14, wherein the camera unit is configured to perform a baseline measurement, which includes a measurement of a first baseline pupillary information of the first eye of the user in response to the first background sound signal, and wherein the processor unit is configured to;

perform pre-processing of the first pupillary information and the first baseline pupillary information for removing artifacts in the first pupillary information and the first baseline pupillary information, provide a normalized first pupillary information based on normalization of the first pupillary information with the first baseline pupillary information, repeat the pre-processing with at least a second baseline pupillary information in response to a second background sound signal and at least the second pupillary information in response to the second sound scene, provide a normalized second pupillary information, and provide the averaged pupillary information based on an average between the normalized first pupillary information and at least the normalized second pupillary information.

16. A hearing device system according to claim 14, wherein the processor unit is configured to;

detect eye-blinks in the pupillary information and in the baseline pupillary information, where the pupillary information and the baseline pupillary information comprises data of pupil size and/or pupil dilation of the first eye, and the eye-blinks are detected as a value of the pupil size being below a pupil size threshold, remove the pupil sizes being below the pupil size threshold from the pupillary information and the baseline pupillary information, and interpolate the removed pupil size.

17. A hearing device system according to claim 14, wherein the hearing aid configuration includes hearing aid settings, optimal mapping parameters of stimulation electrodes connected to a cochlear implant, where the hearing device is a cochlear implant, placement of an ear piece of the hearing device into an ear canal, and/or frequency response of the hearing device.

18. A hearing device system according to claim 14, comprising a hearing aid configuration unit configured to receive a classifier signal comprising the averaged pupillary information and/or a category, such as the first category or the second category, of the averaged pupillary information, wherein the hearing aid configuration unit is configured to automatically and/or continuously adjust the hearing aid configuration based on the category and/or the averaged pupillary information received via the classifier signal.

* * * * *